United States Patent [19]

Cook et al.

[11] Patent Number: 5,587,471
[45] Date of Patent: Dec. 24, 1996

[54] METHOD OF MAKING OLIGONUCLEOTIDE LIBRARIES

[75] Inventors: Phillip D. Cook, Carlsbad; David J. Ecker, Encinitas; Oscar L. Acevedo, San Diego; Peter Davis, Carlsbad, all of Calif.

[73] Assignee: ISIS Pharmaceuticals, Inc., Carlsbad, Calif.

[21] Appl. No.: 179,972

[22] Filed: Jan. 11, 1994

[51] Int. Cl.$^6$ ................................................. C07H 21/00
[52] U.S. Cl. ....................... 536/25.3; 536/25.4; 536/25.41
[58] Field of Search ............................ 435/6; 536/23.1, 536/25.3, 25.4, 25.41

[56] References Cited

U.S. PATENT DOCUMENTS 3,687,808  8/1972  Merigan et al. ......................... 195/28

FOREIGN PATENT DOCUMENTS

WO92/00091  1/1992  WIPO .
WO92/03461  3/1992  WIPO .
WO92/09300  6/1992  WIPO .

OTHER PUBLICATIONS

Anderson et al., "Synthesis of Pyrazolo[3,4-d] Pyrimidine Ribonucleoside 3', 5'-Cyclic Phosphates Related to cAMP, cIMP and cGMP", *Nucleosides and Nucleotides* 6: 853–863 (1987).

Nord et al., "Synthesis, Structure, and Biological Activity of Certain 2-Deoxy-β-D-ribo-hexopyranosyl Nucleosides and Nucleotides", *J. Med. Chem.* 30: 1044–1054 (1987).

Ugarkar et al., "A Simple Oxidation of Formycin to Oxoformycin and Oxoformycin B. Syntehsis of 6-Methyloxoformycin, a C-Nucleoside Analog of Doridosine" *J. Heterocyclic Chem* 21: 1865–1870 (1984).

*Primary Examiner*—David Guzo
*Attorney, Agent, or Firm*—Woodcock Washburn Kurtz Mackiewicz & Norris

[57] ABSTRACT

The present invention provides methods of analyzing and evaluating phosphorus bearing monomeric units as to their suitability for use in preparing randomer oligomer libraries. The invention further provides methods for preparing such randomer oligomer libraries from the selected monomers.

24 Claims, No Drawings

METHOD OF MAKING OLIGONUCLEOTIDE LIBRARIES

FIELD OF THE INVENTION

The invention is related to the field of combinatorial libraries and methods of making the same.

BACKGROUND OF THE INVENTION

There is an increasing need to find new molecules that can effectively modulate a wide range of biological processes. Rational drug design methodologies which have been used historical to design new drugs and other useful compositions, have been limited by the fact that the new drugs are generally derived from a known starting point. Recently, new technologies have focused on non-rational drug design. These methodologies generally rely upon the use of combinatorial libraries of randomly created polymers. Some work has been done to optimize the "randomness" of peptide libraries. Rutter and Santi, U.S. Pat. No. 5,010,175, focuses upon identifying the binding rate constants of amino acid units and modifying incorporation of each amino acid depending upon the rate constant for a given amino acid. Lam, et al., PCT/US91/04666 filed Jul. 1, 1991, teach coupling amino acid units to a solid support, mixing the solid supports, and aliquoting the solid supports into equal portions. Thereafter the coupling, aliquoting, and mixing are repeated. Similarly, Owens, et al., 1991, *Biochem. Biophys. Res. Comm.*, 181, 402–408, teach several coupling reactions each with different amino acids conducted simultaneously and then combined to generate a near equimolar mixture before coupling additional residues. Houghten et al., PCT/US91/08694 filed Nov. 20, 1991, teach a process for the synthesis of a complex mixture pool of solid support-coupled monomeric repeating units, such as amino acids, by reacting the monomeric units with solid supports and mixing the solid supports linked to the monomeric units to form a reaction product pool. Thereafter the reaction pool is separated into a number of aliquots of equal weight and the process is repeated to produce peptides of a desired length.

As compared to amino acids, nucleotide monomers and chemical species related thereto represent a very different class of chemicals having very different properties. These difference are of such extent so as to require very dissimilar chemistries to prepare polymeric species from the monomers. Additionally they present other problems and differences such as purification that must be overcome in the preparation of random libraries. Until now, little work has been done to optimize the preparation and use of nucleotide based combinatorial libraries. Huse, et al., PCT/US91/05939 filed Aug. 20, 1991, teach a method of synthesizing oligonucleotides having random tuplets (i.e. doublets, triplets, or quartets) using individual monomers whereby monomers are sequentially coupled in separate reaction vessels on separate supports. Thereafter the supports are mixed, and the mixture is aliquoted. The tuplets are designed so as to provide the entire genetic code, excepting those degenerate codons.

Methods of reducing bias by equalizing binding of each unit in an oligonucleotide pool are greatly desired. These and other objects are provided by the present invention.

SUMMARY OF THE INVENTION

In some embodiments of the present invention there are provided methods of preparing a random phosphate linked oligomer library comprising selecting a group of phosphorous bearing monomers, testing the group of monomers for chemical suitability and selecting from the group of phosphorous bearing monomers those monomers that are chemically suitable. The selected monomers are reacted with a solid support and the relative coupling efficiency of each phosphorous bearing monomer unit to the solid support is determined. Based upon the determined coupling efficiency, a mixture of the selected phosphorous bearing monomer units is prepared and the mixture is reacted to a solid support or growing oligomer chain. The cycle may be repeated to prepare a random oligomer library in which the oligomers are of a desired length.

In other embodiments of the present invention methods of preparing a random phosphate linked oligomer library are provided comprising selecting a group of phosphorous bearing monomers to be tested, testing the phosphorous bearing monomers for chemical suitability, selecting from the group of phosphorous bearing monomers those monomers that are chemically suitable and individually reacting to completion via phosphate couplings each of the chemically compatible phosphorous bearing monomers with a solid support or growing oligomer chain. Thereafter, all of the solid supports are combined to form a mixture and the mixture is again divided into portions. The cycle is repeated until a random oligomer library comprising oligomers of a desired length is prepared.

The invention further includes oligomeric compounds prepared using the methods of the invention.

DETAILED DESCRIPTION OF THE INVENTION

The present invention provides methods of preparing random oligomer libraries. In accordance with methods of the present invention, a group of phosphorous bearing monomers are selected. The term "phosphorous bearing monomer" as used herein refers to nucleotide monomers comprising a nucleoside and a phosphate moiety that can form a phosphate backbone linkage upon coupling one monomer to the next. Naturally occurring nucleotides such as adenosine, thymidine, cytidine, guanosine and uridine are well known phosphorous bearing monomers. In some preferred embodiments of the present invention nucleotide analogs may also be used. For example purines and pyrimidines other than those normally found in nature may be employed. Suitable purine, pyrimidine and other heterocyclic bases include those disclosed in: U.S. Pat. No. 3,687,808 to Merigan et al., Englisch et al., *Angewandte Chemie*, International Edition, 1991, 30, 613–722 (see especially pages 622 and 623, and the *Concise Encyclopedia of Polymer Science and Engineering*, J. I. Kroschwitz Ed., John Wiley & Sons, 1990, pages 858–859. Monomers having modifications on the furanosyl portion of the nucleotide subunits may also be used as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$, $O(CH_2)_nCH_3$ where n is from 1 to about 10; $C_1$ to $C_{10}$ lower alkyl, substituted lower alkyl, alkaryl or aralkyl; Cl, Br, CN, $CF_3$, $OCF_3$, O-, S-, or N-alkyl; O-, S-, or N-alkenyl; $SOCH_3$, $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyl and glyceryl may also be used in place of the pentofuranosyl group.

This group of monomers is tested for chemical suitability for use in combinatorial chemistry and a sub-group of monomers which are chemically suitable are selected. Chemical suitability can be measured by the following factors. The monomers should be incorporated to roughly the same degree and with sufficient efficiency to give a majority of full-length oligomer product; the product of a coupling reaction is predominantly the desired product; and the monomer should be stable to the selected synthesis and deprotection conditions of the system. In addition, it may be preferable that the monomer have few or no special handling requirements, such as treatment with a special reagent, extended deprotection time, excessively high reaction time, or excessive reagent use. For example, monomers which require lengthy deprotection may not be suitable for use with other monomers which cannot tolerate lengthy deprotection. Incompatibility with an organic base which is necessary for deprotection of one or more additional monomers is also an indication that such monomer is not suitable for a particular use. For example, in one embodiment of the present invention, suitable monomers should react at from about 0.1 to about 0.2M concentration and be amenable to deprotection in concentrated ammonia at 55° C. overnight. Monomers which are not suitable will result in products that include undesirable impurities due to insufficient reactivity or excessive sensitivity to concentrated ammonia treatment.

Once a sub-group of monomers which are chemically suitable have been selected, oligomer libraries may be prepared. In accordance with the present invention, two methods are useful. In one preferred embodiment, mixtures of chemically suitable monomers are prepared. Preferably, phosphoramidites are dissolved in anhydrous acetonitrile to give a solution having a given ratio of amidite concentrations. By creating a mixture of monomers in solution, the mixture can be treated as if it contains only a single monomer on an automated synthesizer, thereby bypassing user interaction during coupling. The mixture of known chemically compatible monomers is reacted to a solid support, or further along, may be reacted to a growing chain of monomer units.

The terminology via "phosphate coupling" as used herein is understood to including effecting a coupling using phosphate $P^v$ coupling (true phosphate coupling) or a coupling using a phosphate precursor such as a $P^{III}$ coupling (a phosphite coupling). Such coupling thus includes the use of amidite (phosphoramidite), triester, H-phosphonate, halide and solution phase couplings. A preferred coupling method is via the so called "phosphoramidite coupling" (a phosphite coupling). In using this coupling method, after the phosphite coupling is complete the resulting phosphite is oxidized to a phosphate. Oxidation can be effected with oxygen to give phosphates or with sulfur to give phosphorothioates.

In each of the methods of the invention, the solid supports which are useful are well known in the art. For example, controlled pore glass (CPG) solid support beads are commonly used. Other useful solid supports that may be used in methods of the present invention include polystyrene resins, derivatized polystyrene resins, graft polymers of polyoxyethylene and polyvinyl alcohol, polyhydroxy-styrene or chloromethylated polystyrene crosslinked with ethylene glycol, oligoethylene glycol, polyacrylate polymer, and polymethacrylate polymer functionalized with hydroxy groups. Polyacrylmorpholide support resins may also be used in some methods of the present invention. Inorganic supports may also be used including silicon based compounds. Of course other solid supports known to those skilled in the art may also be employed in methods of the present invention. Supports useful in methods of the present invention are reactive to monomers useful in methods of the present invention via "standard reactive sites" by which coupling is accomplished. By way of example, a standard reactive site of CPG is a long-chain with a terminal alkyl amine functionality coupled with a deoxynucleoside succinate. The rest of the CPG support being ideally and preferably innate.

In those embodiments of the invention wherein it is desirable not to introduce bias in the oligomer libraries of the invention that are a result of having less than all of the possible combinations of nucleotide sequences, preferably, the number of reactive sites on a particular support will be selected to be greater than the number of sequences to be made by orders of magnitude (at least two orders of magnitude) in order to ensure that all possible sequences are represented adequately. Coupling may be achieved using commercially available automated synthesizers such as ABI 394 automated synthesizer (ABI, Foster City, Calif.) using standard DNA synthesis reagents.

Since a diversity of nucleotides may be used in preparing oligomer libraries, accounting of the coupling efficiencies of the individual nucleotides may be practiced to eliminate any bias that may be introduced in the oligomer libraries. To mitigate for such bias, the relative incorporation rates of monomers are determined by coupling monomers to supports treated with a nucleotide of interest that is chosen as a standard. The product is analyzed, for instance, by the methods of reverse phase HPLC or capillary gel electrophoresis. For example, peaks in the HPLC chromatograph corresponding to different dinucleotide phosphates are identified and converted to relative molar amounts using the known extinction coefficients at 260 nm ($\epsilon_{260}$) or other selected wave length. In practicing certain embodiments of the invention, for the incorporation of a nucleotide analog having modifications that do not change the base ring and do not have any inherent absorbance at 260 nm, the nucleotide analogs are assumed to have the same $\epsilon_{260}$ as the parent DNA or RNA nucleoside. In practicing other embodiments of the invention, an extinction coefficient, as for example that at 260 nm, will be determined experimentally using standard spectrophotometric techniques. In practicing further embodiments, the extinction coefficient can be determined by the following method.

It has been determined that coupling efficiency, estimation of extinction coefficient and evaluation of coupling product quality for any phosphate-bearing monomeric unit can be effected by using standard phosphoramidite coupling chemistry and "standards" such as dT-CPG DNA synthesis support. This includes the commercially available DNA or RNA amidites, as well as like compounds that are useful in oligomer synthesis. Using dT as a symbol for thymidine, dC as a symbol for deoxy cytidine and other abbreviations as note in the text below, in practicing my methods, for example, the standard, deoxythymidine derivatized controlled-pore glass (dT-CPG) is used as a solid phase synthesis medium, and unreactive 5'-O-acetyldeoxycytidine-derivatized controlled-pore glass (5'-O-Ac-dC-CPG) is used as an "internal reference standard". These could be substituted with any pair of entities, provided that both are compatible with the desired chemistry, both are strong chromophores of known or measurable extinction coefficient at a useful wavelength, and one is reactive while the other is inert to the coupling conditions. The method can be expanded to include other coupling methods and other solid supports that can be analyzed by equivalent means different that those used for illustrative purposes in the examples below. Other examples would include phosphate triester coupling and hydrogen phosphonate coupling.

Thus, in accordance with methods of the present invention, reactive dT-CPG (a standard) is mixed with a lesser molar equivalent of unreactive 5'-Ac-dC-CPG (internal reference standard). The unreactive 5'-Ac-dC-CPG internal standard allows for accurate determination of unreacted thymidine, i.e. dT, present before and after a coupling reaction.

The peak area of dT in a HPLC chromatogram can be identified as $A_T$ and the peak area of deoxycytidine in the chromatogram can be identified as $A_C$. The initial ratio of peak areas for dT and dC is $(A_T/A_C)_0$. Relative moles of dC can be identified as C, and relative moles of dT can be identified as T. These are calculated from peak areas, $A_C$ and $A_T$, respectively, using known extinction coefficients: $C=A_C/\epsilon_C$ and $T=A_T/\epsilon_T$. Thus the relative peak area or molar amount of dT initially present can be calculated from $A_C$:

$$
\begin{aligned}
A_{T0} &= (A_C)[(A_T/A_C)_0] \\
T_0 &= (C)[(T/C)_0]
\end{aligned}
$$

also, $$
\begin{aligned}
(C)(T/C) &= (A_C/\epsilon_C)[(A_T/\epsilon_T)/(A_C/\epsilon_C)] \\
&= (A_C/\epsilon_C)(A_T/A_C))(\epsilon_C/\epsilon_T)
\end{aligned}
$$

thus, $$
\begin{aligned}
(C)[(T/C)_0] &= (A_C/\epsilon_C))[(A_T/A_C)_0](\epsilon_C, \epsilon_T) \\
&= (A_C/\epsilon_T)[(A_T/A_C)_0]
\end{aligned}
$$

An amidire monomer of interest, identified as X, is reacted with an aliquot of the CPG mixture. Reacted CPG is cleaved and deprotected with ammonia, then analyzed by HPLC to determine the area under the peak for dC, i.e. $A_C$; area under the peak for unreacted dT, i.e. $A_{Tur}$; and area under the peak for X-T dimer, i.e. $A_{XT}$. These values are used to calculate coupling efficiency, C.E.; and X-T dimer extinction coefficient, $\epsilon_{XT}$.

The coupling efficiency, C.E., is defined by the ratio of reacted dT, i.e. $T_r$, to total dT, i.e. $T_0$. Thus C.E.=$T_r/T_0$. Coupling efficiency can be determined from the relative moles of unreacted dT present before, i.e. $T_0$, and after, i.e. $T_{ur}$, coupling with X; all three are related by the equation $$T_0 = T_r + T_{ur}.$$

Since C.E. is a unitless value, HPLC peak areas can be used instead of relative molar quantities to perform the calculation:

$$
\begin{aligned}
C.E. &= (T_r/T_0) \\
&= (T_0/T_0) - (T_{ur}/T_0) \\
&= 1 - (T_{ur}/T_0) \\
&= 1 - (A_{Tur}/\epsilon_T)/(A_{T0}/\epsilon_T) \\
&= 1 - (A_{Tur}/A_{T0}) \\
&= 1 - (A_{Tur})/[(A_C)[(A_T/A_C)_0]]
\end{aligned}
$$

(which are all measurable quantities)

The extinction coefficient $\epsilon$ for X, i.e. $\epsilon_{XT}$, in the given HPLC solvent system is determined from the C.E. for X and the relative areas of the HPLC peaks. The amount of X-T is equal to the amount of T that has reacted. $\epsilon$ for dimer X-T is defined as the peak area $A_{XT}$ divided by the moles of X-T dimer present XT, and is calculated as follows:

$$
\begin{aligned}
XT &= T_r \\
&= (C.E.)(T_0) \\
\epsilon_{XT} &= (A_{XT}/XT) \\
&= (A_{XT})/(C.E.)(T_0) \\
&= (A_{XT})/(C.E.)(C)[(T/C)_0] \\
&= (A_{XT})/(C.E.)(A_C/\epsilon_T)[(A_T/A_C)_0]
\end{aligned}
$$

(which again are all measurable quantities)

Finally, the quality of the coupling-product X-T can be evaluated from the appearance of the HPLC chromatogram. Other significant peaks (those summing >10% of product-peak area) can also be addressed. Often they are the desired X-T dimer that retains protective groups. Disappearance of these peaks with extended ammonia treatment will confirm that the monomer requires extended ammonia deprotection beyond the standard time. In other cases the extra peaks can be identified as undesirable side-products and in some cases they cannot be identified. Generally, coupling efficiency of less than about 90%, a required ammonia deprotection time of greater than a few days, or the occurrence of side-products amounting to greater that 10% (by UV absorbance) can be selected as initial guidelines to judge the possibility of excluding an amidite from consideration for use in a particular set of amidires used in generating random oligomeric compounds.

Given the relative incorporation rate, a phosphorous bearing monomer mixture can be adjusted to improve the incorporation rate in order to move towards a desired relative concentration. One preferred relative concentration is an equimolar concentration. In other preferred embodiments of the present invention one or more monomers may be preferentially incorporated by adjusting the ratio of monomers in the mixture in accordance with their relative incorporation rates. Such mixtures that take into account relative incorporation rates are referred to herein as "adjusted" mixtures. For the purposes of this specification, it is assumed that the incorporation is linear with respect to rate constant and concentration. Thus, the relative incorporation rate of monomers that react more slowly can be improved by increasing the relative concentration of the monomer in an adjusted mixture. Accordingly, the relative volumes of each monomer in the adjusted mixture are the inverse proportion of the relative concentration.

Once the relative incorporation is determined, the amidire mixture is then tailored to improve the relative incorporation rate and make it closer to equimolar. In doing this, as a first approximation, it is assumed that the incorporation is linear with respect to rate constant and concentration, so that the relative incorporation residues that react more slowly can be improved by increasing the relative concentration in a new mixture. The relative volumes of each amidite in the next mix are the inverse proportion of the relative concentration.

In practicing the invention, in some instances only a single optimization cycle need be practiced. In other instances, e.g. with nucleotides have widely divergent initial relative incorporation rates, adjustment to normalize the relative incorporation may be performed more than once in order to optimize normalization within desired limits.

In some embodiments of the invention where equimolar incorporation is desired, acceptable limits for unequal incorporation may generally be +/−10%. In such cases, at no time will the difference between the most and least incorporated residue be more than 20%. For example, a normalized ratio of 1.1/1.0/1.0/0.9 is acceptable. However, a normalized ratio of 1.15/1.0/0.95/0.9 may not acceptable in some cases. In this last instance a further adjustment iteration may be effected to bring the rates of incorporation within the set limit.

Of course, where equimolar incorporation is not desired, and instead a fixed, rather than random, position is sought, monomer mixtures should be replaced with a "fixed" monomer. Fixed, as used herein is meant to refer to monomers within an oligomer which are known, set or otherwise predetermined. Accordingly, in the oligonucleotide NNNNGNNN the fifth position is a fixed position which has been predetermined to be a guanosine while the remaining positions may be, randomly, any of the monomers making up the monomer mixture, the resultant library being all combinations of selected monomers with the proviso that guanosine is the fifth residue.

As used herein, a random oligomer is an oligomer having at least one random position. A fixed position may be incorporated into such random oligomers in accordance with methods of the present invention, by use of the appropriate monomer for incorporating the fixed position within the oligomer during a coupling step. If more than one fixed position is desired, each fixed position is introduced stepwise by use of the appropriate monomer during a coupling step. If more than one fixed position is desirable, such fixed positions can be adjacent to one another in the oligomer sequence or they can be separated in the oligomer sequence by random positions. Whether fixed or random, each position in an oligomer of desired length is added via an iteration of the coupling steps. These steps are repeated until an oligomer library comprising oligomers of a desired length are prepared.

Random phosphate linked oligomer libraries can also be prepared by individually reacting, to completion, each of a selected group of chemically suitable phosphorous bearing monomers with a solid support or growing nucleotide chain using phosphate coupling. Monomers which are coupled one at a time in a non-competitive nature are assumed to couple to completion. Therefore the factors involved in creating equal incorporation are (i) sufficient inherent coupling efficiency for all monomers used and (ii) equal amounts of solid support (reactive sites) for each of the individual coupling reactions. Completeness of a reaction can be monitored for example, by standard DMT-cation assay. Alternately, a post-synthesis analysis can be used to determine how well monomers were incorporated during the synthesis.

Random oligomer pools may be prepared in accordance with this embodiment of the invention by preparing a number of individual aliquots of solid support equal to the number of individual types of monomers which are to be incorporated into the random oligomer library. Thereafter, each of the aliquots is reacted with a different monomer until the reaction goes to completion. The aliquots are thoroughly mixed and apportioned into a number of aliquots equal to the number of unique monomers to be incorporated during this next step. The apportionment and coupling steps may be performed until an oligomer library comprising oligomers of desired length is prepared.

In a preferred embodiment of the invention that is a variation of the immediately proceeding procedure, one or more fixed positions can be introduced into the oligomer library by refraining from dividing the solid support during one or more of the iterations of the procedure. During the iteration of the procedure wherein the fixed position is introduced, the totality of the solid support is reacted with the monomer that is desired at the fixed position. This can be repeated if more than one consecutive fixed position is desired. If the fixed position (or positions) are desired at the end of the oligomer, synthesis is halted after the iteration that introduced the fixed position (or positions). However, if additional random positions are desired after the fixed position (or positions), after introduction of the fixed position (or positions) during the next iteration of the procedure, once again the solid support is divided into aliquot and each aliquot reacted with a different monomer.

In a further preferred embodiment of the invention, one or more "fixed positions" may also be incorporated into a randomized oligomer by reacting individual monomers to aliquots of the support, but refraining from mixing the aliquots. Instead, the aliquots are kept separate and each sub-set, or pool, is further divided into the proper number of portions corresponding to the number of monomers to be reacted. Each portion of support is then reacted with a different monomer, followed by mixing and reapportionment of the support within each pool. Repeating this cycle for each of the different sub-sets of supports results in randomization in positions following the fixed position in the sequence. By keeping the pools separate, one obtains separate pools which are unique for one or more monomers at one or more the fixed positions.

In a further preferred embodiment, that can be considered as a variation of the above embodiments, one of the positions introduced is a "null" position—that is it is an "empty" or "nothing" position. This introduced the ability of the random library to address "length-space" as well as "sequence-space." In practicing this embodiment, in one or more iteration of the process, the solid support is divided into a number of aliquots that is one greater than the number of monomer that are to be reacted. One of the aliquots of the solid support is set aside and is not reacted with monomer during a selected iteration of the process. This aliquot is thereafter returned to the pool of aliquots when the set of aliquots of the solid support are recombined. The resulting oligomer pools contain sequences that vary both in sequence and length. The variation in length can be controlled by the number of positions, i.e. times, in which the null position is introduced, from zero positions to give all full-length oligomers, to all positions to give oligomers of length 1 to full-length.

In an even further preferred embodiment, that can be also considered as a variation of the above "fixed positions" embodiments, the "fixed" position that is introduced is a "negative fixed position" with respect to one of the monomer—that is the position is selected to not contain a particular monomer. This introduces the ability of the random library to address the absence of a particular monomer at a given position in the resulting oligomer. In practicing this embodiment, in one or more iteration of the process, the solid support is divided in to a number of aliquots that is one less than the number of monomers that are to be reacted. The monomer that is to be absent from the known position is not reacted with one of the aliquots of the solid support while the remaining variable monomers are. After the iteration that excludes the selected monomer is competed, the aliquots of the set of aliquots of the solid support are recombined and further iterations (or termination) of the oligomer is effected.

Random oligomer libraries are useful as is described, for example, in published PCT application WO/93/04204. Further random oligomers libraries are useful as is described in concurrently filed patent application entitled "PYRROLIDINE MONOMERS AND OLIGOMERIC COMPOUNDS" also identified by Attorney Docket Number ISIS-1237, commonly assigned with this application.

EXAMPLE 1

Determination of Coupling Efficiency and $\epsilon_{260}$ of Novel Residues

A. Preparation of Solid Support Mixture

5'-O-Ac-dC-support+dT-support was made by first preparing the dC support that was rendered unreactive by removing the 5'-terminal dimethoxytrityl group (i.e. a DMT group) and "capping" the 5'-hydroxyl with an acetyl group in accordance with the following procedure. 1 gram of dC-support (48 μmole dC per gram support, catalog #dC200502, CPG Inc., Fairfield, N.J.) was treated with several aliquots of standard deblock solution, 3% trichloroacetic acid in dichloromethane (approximately 50–70 ml total). This was repeated over several minutes until no more orange color appeared. The support was rinsed well with dichloromethane, ethanol, and diethyl ether and dried under vacuum. The support was then treated with 5 ml each of acetic anhydride and N-methyl imidazole capping solutions (ABI Cap A reagent solution, acetic anhydride in THF, catalog #400234, and ABI Cap B reagent solution, N-methyl imidazole in THF, catalog #400777, both from Applied biosystems, Foster City, Calif.). The slurry was shaken in a sealed vial for 20 minutes, filtered, and the support rinsed with acetonitrile, ethanol, and ether. The support was air dried then vacuum dried.

0.25 g of 5'-O-Ac-dC-CPG was mixed with 1 g of dT-CPG (40 μmole/gram support, dT CPG support catalog #dT200504, CPG Inc., Fairfield, N.J.) to give a dC to dT molar ratio of approximately 1:4. Two aliquots of the mixture were treated with deblock solution on the synthesizer to remove the DMT groups, then treated with concentrated ammonia in a sealed vial at 55° C. for 30 minutes to cleave nucleosides from the support and remove exocyclic amine protecting groups. The supernatant was cooled, dried, reconstituted in 0.1M ammonium acetate, pH 7, and analyzed on a reversed-phase HPLC column (Water Delta Pak C18 300 Å, catalog # 035571, Millipore Corp., Milford, Mass.) using a gradient of 1% to 16% acetonitrile in 0.1M ammonium acetate, pH 7, over 22.5 minutes. The HPLC system is a Waters 991 detector, 625 LC pump, and 715 WISP autoinjector (Millipore, Corp.). Calculations were performed using data collected at a wavelength of 260 nm.

B. Determination of Coupling Efficiency and Dimer Extinction Coefficient

Synthesis of dimers was performed with an ABI 394 DNA synthesizer (Applied Biosystems, Foster City, Calif.) using standard DNA synthesis reagents and synthesis protocols, with the exception of an extended (5 minute) coupling time added to the synthesis cycle. 1 μmole of synthesis support from Example 1A was used. Oligomers were cleaved from solid support by treatment with concentrated ammonia for 2 hours at 20° C. The supernatant was removed from the support and heated in a sealed vial at 55° C. for two hours. This solution was cooled, and most of the ammonia removed by evaporation. Oligomers were analyzed directly on reversed-phase HPLC column (Waters Nova-Pak Phenyl, cat. # 10656, Millipore, Corp.) using a gradient of 1% to 46% acetonitrile in 0.1M ammonium acetate, pH 7, over 30 minutes and the HPLC system described previously.

Coupling efficiency of 2'-O-pentyladenosine phosphoramidire and extinction coefficient for the resulting dimer were calculated from peak-areas as described previously:

$$C.E. = 1 - \{A_{T\alpha T}/[A_C(A_T/A_C)_0]\}$$
$$= 1 - \{2.87/(7.03)(5.57)\}$$
$$= 0.927(92.7\%)$$

$$\epsilon_{XT} = A_{XT}/(C.E.)(A_C/\epsilon_T)[A_T/A_C)_0]$$
$$= 86.77/(.927)(7.03/8.7)(5.57)$$
$$= 20.8 M^{-1}cm^{-1}(10^3)$$

The coupling efficiency of 92.7% exceeds the desired 90% lower limit described previously. The calculated extinction coefficient of 20.8 compares favorably to the published value of a DNA dA-dT of 22.84.

EXAMPLE 2

An equimolar mixture of four DNA amidites (mG, 2'-O-methyl guanosine; mA, 2'-O-methyl adenosine; biA, 2'-O-butylimidazolyl adenosine; and nC, 2'-O-nonyl cytidine) was coupled to dT-CPG mix as described in Example 1. The results of these couplings are as shown in Table I. The initial unequal incorporation favors biA and disfavors nC as is shown in the third column. To mitigate this, the relative amount of nC amidite is increased by the inverse of the relative incorporation as is shown in the fourth column and is normalized for the particular volume, i.e. 400 μl, in the fifth column. The new adjusted mixture is shown in the sixth column and for the next coupling the relative incorporations are nearly equal as is seen in the seventh column.

TABLE I

| nucleo-tide | amount 0.1M (ul) | relative incor-poration for 1:1 mixture | (relative-incorpor-ation)$^{-1}$ | * | new amount (0.1M (μL) | new incor-poration |
|---|---|---|---|---|---|---|
| mA | 100 | 1.38 | 0.73 | ×93.7 | 68 | 1.02 |
| mG | 100 | 0.98 | 1.02 | ×93.7 | 95 | 0.90 |
| biA | 100 | 0.97 | 1.03 | ×93.7 | 96 | 1.10 |
| nC | 100 | 0.67 | 1.49 | ×93.7 | 140 | 0.97 |

*normalized to give 400 μl total volume

EXAMPLE 3

Noncompetitive Homogeneous Coupling Method for the Preparation of Oligonucleotides with "Fixed" positions.

16 μM of dT-CPG solid support was divided into four equal 4 μM aliquots. Each aliquot was reacted with 17 equiv. of one of 2'-O-methyl adenosine (mA), 2'-O-methyl guanosine (mG), 2'-O-butylimidazolyl adenosine (biA), or 2'-O-nonyl cytidine (nC) amidites until completion using standard solid state synthesis coupling cycles. The extent of reaction was determined to be at least 90% completed, as described previously in Example 1B. The aliquots were mixed thoroughly and again divided into four equal aliquots. Each aliquot was reacted with 17 equiv. of one of the 2'-O-methyl adenosine (mA), 2'-O-methyl guanosine (mG), 2'-O-butylimidazolyl adenosine (biA), or 2'-O-nonyl cytidine (nC) amidites, as above, until completion. The cycle was repeated three times for a total of three random positions.

The 16 μM of CPG solid support was divided into four equal 4 μM aliquots. Each aliquot was reacted with 17 equiv. of one of 2'-O-methyl adenosine (mA), 2'-O-methyl guanosine (mG), 2'-O-butylimidazolyl adenosine (biA), or 2'-O-nonyl cytidine (nC) amidire until completion. The aliquots were not mixed, but kept separate to obtain a unique residue in the fifth position of each of the four pools.

Thereafter each of the four aliquots were divided into four subsets of 1 μM. One subset from each aliquot was reacted with one of 17 equiv. of one of 2'-O-methyl adenosine (mA), 2'-O-methyl guanosine (mG), 2'-O-butylimidazolyl adenosine (biA), or 2'-O-nonyl cytidine (nC) amidites until completion using standard solid state synthesis coupling cycles. The subsets from each aliquot were mixed together, resulting in four aliquots. Thereafter the four aliquots were apportioned into sub-sets and each subset of each aliquot is again reacted with one of 2'-O-methyl adenosine (mA), 2'-O-methyl guanosine (mG), 2'-O-butylimidazolyl adenosine (biA), and 2'-O-nonyl cytidine (nC) amidires until completion using standard solid state synthesis coupling cycles. This procedure was repeated three times for a total of three more random positions. There was a final reaction with dT amidire to give all of the four pools a 5'-terminal dT. The resultant four randomer oligonucleotide pools each have a 3'-terminal dT, followed by three random positions, a fixed monomer (either mA, mG, biA, or nC) in the fifth position, three more random positions, and finally a 5'-terminal dT. This is represented by the sequence notation 5'-TNNNXNNNT, in which N are random positions and X is a unique fixed position.

EXAMPLE 5

Post Synthesis Analysis

A typical digestion/HPLC analysis was performed as follows. For each digestion 1 μL each of Nuclease P1 (BRL, 33 units/μL), bacterial alkaline phosphatase (BAP) (BRL, 150 units/μL), and snake venom phosphodiesterase (SVP) (Pharmacia, 0.1 units/μL) was added to 2 μL of 10× buffer (140 mM $MgCl_2$, 720 mM NaCl, 500 mM tris-HCl pH 8.5) and 13 μL water. 2 μL of oligonucleotide (1 mM in strands; 0.2 $A_{260}$ units) was added for a total volume of 20 μL, and the mixture was incubated at 37° C. overnight.

After incubation, 2.5 volumes (60 μL) of methanol was added to each digestion (to prevent selective binding of lipophilic nucleosides during ultrafiltration) and each was mixed well. The supernatant was passed through a centrifugal 10,000 NMW cut-off ultrafilter (Millipore, #UFC3 TGC 00) to remove enzymes, dried by evaporation, dissolved in HPLC starting mobil-phase, and analyzed by HPLC (0–90% B in A over 40 minutes) at 260 nm.

For the oligonucleotide TNNNXNNNT, in which X=2'-O-butylimidazolyladenosine (biA), and each N is one of 2'-O-methylguanosine (mG), 2'-O-methyladenosine (mA), 2'-O-butylimidazolyladenosine (biA), or 2'-O-nonylcytidine (nC), the expected and experimental ratios are summarized in Table II.

TABLE II

| monomer | expected relative ratio | experimental relative ratio | normalized experimental relative ratio exper./expec. |
| --- | --- | --- | --- |
| dT | 2.00 | 2.16 | 1.08 |
| mG | 1.50 | 1.67 | 1.12 |
| mA | 2.50 | 2.67 | 1.07 |
| biA | 1.50 | 1.29 | 0.86 |
| nC | 1.50 | 1.21 | 0.81 |

This result shows that all four residues were well represented in nearly equal proportions in the oligonucleotide pool.

What is claimed is:

1. A method of preparing a random phosphate linked oligomer library comprising:
   (a) selecting a group of phosphorous bearing monomers;
   (b) testing said group of monomers for chemical suitability with respect to at least one predetermined parameter;
   (c) selecting from said group of phosphorous bearing monomers a sub-group of monomers that are chemically suitable with respect to said predetermined parameter;
   (d) reacting each of the monomers of said sub-group of monomers to a standard reactive site located on a solid support;
   (e) analyzing the relative coupling efficiency of each of said monomers of said sub-group of monomers with said standard reactive site;
   (f) preparing a mixture of said monomers of said sub-group of phosphorous bearing monomers adjusted in accordance with coupling efficiencies determined in step (e);
   (g) reacting via phosphate coupling said adjusted mixture of phosphorous bearing monomers of said sub-group to a solid support or growing oligomer chain; and
   (h) repeating step (g) in order to prepare a random oligomer library comprising oligomers of a desired length.

2. The method of claim 1 further including:
   selecting an internal reference standard; and
   adding said internal reference standard to said solid support having said standard reactive site prior to reacting said monomers of said sub-group to said standard reactive site.

3. The method of claim 1 wherein said predetermined parameters are selected from the group consisting of degree of incorporation, efficiency of incorporation, predominance of a desired product, compatibility of synthesis conditions, deprotection conditions, standard solubilizing reagent requirements, standard coupling reagent requirements, non-excessive reagent usage, non-excessive reaction time, non-excessive deprotection time, and non-compatible acid or base conditions.

4. The method of claim 1 further including selecting said solid support in said step (g) to have a number of reactive sites that is at least two orders of magnitude greater than the number of the individual nucleotides in any of said oligomers that will make up said oligomer library.

5. The method of claim 1 wherein the relative coupling efficiency of said monomers of said sub-group is analyzed by determining a relative incorporation with respect to a standard, taking the inverse of said relative incorporation, and normalizing said inverse of said relative incorporation with respect to the totality of said members.

6. The method of claim 1 including repeating at least one further iteration of steps (d) and (e) using the determined coupling efficiency of a previous step (e) to calculate a new coupling efficiency for the further iteration.

7. The method of claim 1 further including incorporating at least one fixed position in said growing oligomer by:
   reacting via phosphate coupling a single one of said monomers of said sub-group to said solid support or growing oligomer chain.

8. The method of claim 1 wherein the phosphate coupling is selected from the group consisting of amiditc, triester, H-phosphonate, halide and solution phase phosphate coupling.

9. The method of claim 3 wherein said predetermined parameters are selected from the group consisting of degree of incorporation, efficiency of incorporation, predominance of a desired product, compatibility of synthesis conditions, and compatibility of deprotection conditions.

10. A method of preparing a random phosphate linked oligomer library comprising:
   (a) selecting a group of phosphorous bearing monomers;
   (b) testing said group of monomers for chemical suitability with respect to at least one predetermined parameter;
   (c) selecting from said group of phosphorous bearing monomers a sub-group of monomers that are chemically suitable with respect to said predetermined parameter;
   (d) reacting each of the monomers of said sub-group of monomers to a standard reactive site located on a solid support;
   (e) analyzing the relative coupling efficiency of each of said monomers of said sub-group of monomers with said standard reactive site;
   (f) selecting a quantity of solid support;
   (g) dividing said solid support into aliquots, the number of said aliquots equal to the number of said monomers of said sub-group;
   (h) reacting via a phosphate coupling each of said monomers of said sub-group of phosphorous bearing monomers in accordance with coupling efficiencies determined in step (e) with one of said aliquots of said solid support to attach said monomers to said solid support or to attach said monomers to a growing oligomer chain located on said solid support;
   (i) mixing each of said aliquots of said solid support together; and
   (j) repeating steps (g), (h) and (i) in order to prepare a random oligomer library comprising oligomers of a desired length.

11. The method of claim 10 further including:
   selecting an internal reference standard; and
   adding said internal reference standard to said solid support having said standard reactive site prior to reacting said monomers of said sub-group to said standard reactive site.

12. The method of claim 10 wherein said predetermined parameters include degree of incorporation, efficiency of incorporation, predominance of a desired product, compatibility of synthesis conditions, deprotection conditions, standard solubilizing reagent requirements, standard coupling reagent requirements, non-excessive reagent usage, non-excessive reaction time, non-excessive deprotection time, or non-compatible acid or base conditions.

13. The method of claim 10 further including selecting said solid support in said step (f) to have a number of reactive sites that is at least two orders of magnitude greater than the number of the individual nucleotides in any of said oligomers that make up said oligomer library.

14. The method of claim 10 wherein the relative coupling efficiency of said monomers of said sub-group is analyzed by determining a relative incorporation with respect to a standard, taking the inverse of said relative incorporation, and normalizing said inverse of said relative incorporation with respect to the totality of said monomers.

15. The method of claim 10 including repeating at least one further iteration of steps (d) and (e) using the determined coupling efficiency of the prior step (e) to calculate a new coupling efficiency for the further iteration.

16. The method of claim 10 further including incorporating at least one fixed position in said growing oligomer by:
   reacting a single one of said monomers of said sub-group to said solid support or growing oligomer chain.

17. The method of claim 10 further including incorporating at least one null position in a portion of said growing oligomer by:
   dividing said solid support into aliquots, the number of said aliquots equal to one more than the number of said monomers of said sub-group; and
   reacting via a phosphate coupling each of said monomers of said sub-group of phosphorous bearing monomers in accordance with coupling efficiencies determined in step (e) with one of said aliquots of said solid support such that one of said aliquots is left unreacted.

18. The method of claim 10 further including incorporating at least one position in said growing oligomer that excludes at least one of said monomers of said sub-group by:
   dividing said solid support into aliquots, the number of said aliquots equal to less than the number of said monomers of said sub-group; and
   reacting via a phosphate coupling less than all of said monomers of said sub-group of phosphorous bearing monomers in accordance with coupling efficiencies determined in step (e) with one of said aliquots of said solid support.

19. The method of claim 10 wherein the phosphate coupling is selected from the group consisting of amidire.

20. The method of claim 12 wherein said predetermined parameters include degree of incorporation, efficiency of incorporation, predominance of a desired product, compatibility of synthesis conditions, or deprotection conditions.

21. A method of analyzing monomers for suitability of use in preparing oligomers comprising:
   (a) selecting a first monomer-solid support couple, said first monomer-solid support couple selected such that said monomer is a monomer that is reactive for oligomeric synthesis on said solid support;
   (b) selecting a second monomer-solid support couple, said second monomer-solid support couple selected such that said second monomer is a monomer that is non-reactive for oligomeric synthesis on said solid support;
   (c) mixing said first and said second monomer-solid support couples in a known gross ratio;
   (d) determining the exact ratio of said first and second monomers in said mixture;
   (e) selecting a further monomer;
   (f) reacting said further monomer with said mixture to couple said further monomer and said first monomer;
   (g) determining the relative amounts of the products resulting from said reaction of said further monomer with said mixture; and
   (h) either: (1) calculating from said relative amounts of said products and said exact ratio of said first and second monomers in said mixture at least one of: (i) one coupling efficiency of said further monomer; or (ii) an extinction coefficient of the coupling product of said further monomer with said first monomer; or (2) determining from said relative amounts of said products and said exact ratio of said first and second monomers in said mixture the presence of products other than the expected coupling product of said further monomer.

22. The method of claim 21 wherein said determination of said exact ratio of said first and second monomer is effected using the extinction coefficients of said monomers.

23. The method of claim 21 wherein said determination of said relative amounts of the products resulting from said reaction of said further monomer with said mixture is effected by analysis of the peak area of a HPLC chromatogram of said products.

24. The method of claim 23 wherein said products are liberated from said solid support prior to said HPLC analysis.

* * * * *

UNITED STATES PATENT AND TRADEMARK OFFICE
CERTIFICATE OF CORRECTION

PATENT NO. : 5,587,471
DATED : December 24, 1996
INVENTOR(S) : Phillip D. Cook et al It is certified that error appears in the above-identified patent and that said Letters Patent is hereby corrected as shown below:

Col. 14, line 28, "amidire" should read --amidite, triester, H-phosphonate, halide and solution phase phosphate coupling--.

Signed and Sealed this

Third Day of November, 1998

Attest:

BRUCE LEHMAN

Attesting Officer     Commissioner of Patents and Trademarks